United States Patent [19]

D'Alelio, deceased et al.

[11] Patent Number: 4,520,198

[45] Date of Patent: May 28, 1985

[54] VINYLACETYLENE-TERMINATED POLYIMIDE DERIVATIVES

[75] Inventors: Gaetano F. D'Alelio, deceased, late of South Bend, Ind., by St. Joseph Bank and Trust Company, executor; Phillip A. Waitkus, Sheboygan, Wis.

[73] Assignee: Plastics Engineering Company, Sheboygan, Wis.

[21] Appl. No.: 565,393

[22] Filed: Dec. 27, 1983

Related U.S. Application Data

[60] Division of Ser. No. 353,871, Mar. 2, 1982, Pat. No. 4,435,323, and a continuation-in-part of Ser. No. 199,616, Oct. 22, 1980, abandoned.

[51] Int. Cl.$^3$ ............... C07D 209/34; C07D 471/00; C08F 22/40
[52] U.S. Cl. .................................. 546/66; 525/279; 526/262; 548/423; 548/431; 548/433
[58] Field of Search ............... 526/262; 525/279; 546/66; 548/423, 431, 433, 473, 416

[56] References Cited

U.S. PATENT DOCUMENTS 3,929,713 12/1975 D'Alelio .............................. 526/262
4,251,417 2/1981 Chow et al. ...................... 260/326 C
4,255,303 3/1981 Antonoplos et al. ............ 260/326 C

*Primary Examiner*—Harry Wong, Jr.
*Attorney, Agent, or Firm*—Walter J. Monacelli

[57] ABSTRACT

Novel, unsaturated vinylacteylene-terminated polyimides and processes for their preparation are disclosed herein. These new polyimides are derivatives of anhydride-terminated aromatic polyimides from which they can be prepared by amidation to provide new unsaturated amide groups having a terminal group containing the structure —CH=CH—C≡C— or —C≡C—CH=CH—, hereinafter sometimes referred to as "conjugated enynes". These new compositions are more tractable than the original anhydride-terminated polyimides and can be converted at appropriate lower temperatures to crosslinked, insoluble, infusible polymers without by-product formation, thereby extending greatly the applications for which the aromatic polyimides can be employed. Moreover, these new polyimides can undergo the Diels-Alder type of addition with a large number of dienophiles. Certain monomeric materials are also described.

24 Claims, No Drawings

VINYLACETYLENE-TERMINATED POLYIMIDE DERIVATIVES

This application is a divisional of copending application Ser. No. 06/353,871, filed Mar. 2, 1982, now U.S. Pat. No. 4,435,323, and a continuation-in-part of application Ser. No. 06/199,616, filed Oct. 22, 1980, now abandoned.

BACKGROUND OF THE INVENTION

1. Field of the Invention

The invention relates to new polymeric compositions derived from aromatic polyimides containing terminally unsaturated groups. More specifically, it relates to such polymers derived from polyimide compositions in which the terminal groups are moieties that contain terminal enyne functions capable of polymerizing and forming crosslinked polymers. Still more specifically, it relates to such crosslinked polymers obtained therefrom without the formation of by-products.

2. State of the Prior Art

Polyimides, as prepared from aromatic dianhydrides and aromatic diamines, are known to have the desired property of high heat resistance and high solvent resistance. Such polyimides, upon condensation to an infusible condition, generate by-products such as water and other vapors or gases which introduce voids into the fabricated products that detract from the expected good physical properties. In addition, because of these same desirable properties, they are untractable and, therefore, very difficult and expensive to work into desired shapes and forms.

Recent patents, such as U.S. Pat. Nos. 3,845,018, 3,864,309, 3,879,395 and 3,998,786 are directed to improving the tractability of the aromatic polyimides by attaching various terminal groups to polyimide oligomers whereby the chains are extended by coupling of the terminal groups. In these patents the coupling groups are attached as terminal imide moieties containing vinyl, ethynyl, nitrile, etc. groups. Thus the terminal anhydride group is converted to an imide group containing a vinyl, nitrile, ethynyl, etc. group. However, in none of these patents nor in any other related prior art references, has there been found any reference or disclosure that the terminal anhydride group on each end could be converted to a terminal imide group containing a vinylacetylenic or enyne moiety possessing a —CH=CH—C≡C— or interchangeably a —C≡C—CH=C— structure.

Previous publications (A. L. Landis, et al, Polymer Preprints 15, 533 (1974), 15, 537 (1974)) describing acetylene-terminated polymers assumed that the cure reaction involved a simple trimerization of three terminal acetylenic end-groups into an aromatic crosslink, thus:

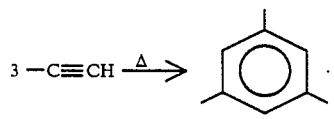

When model compounds, such as phenyl acetylene and others are subjected to "cure" conditions (Technical Report AFML-TR-76-71 June 1976, pp. 8-11, 21-22), they do not give rise to the formation of significant quantities of trimerized products as has been assumed. In addition to major amounts (90%) of polymeric material, there is isolated small quantities of complex mixture of products. It has been shown that terminated acetylene groups can simultaneously react by a number of alternate routes, such as by:

1. Glaser coupling (G. Glaser, Ann. 137, 154 (1870), (which in the presence of air is referred to as oxidative coupling):

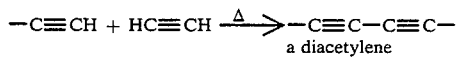
a diacetylene

2. Strauss coupling (F. Straus Ann. 342, 190 (1905))

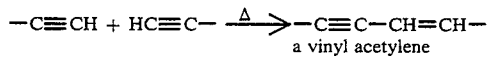
a vinyl acetylene

3. Straus or Glaser product reaction (Chemistry of Acetylenes, H. G. Viehe, ed., Marcel Dekker, N.Y. 1969):

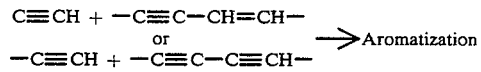

In order to determine the possibility that Straus or Glaser linkages are initially formed which then undergo further reaction and rearrangements, the model compounds

| $\phi C\equiv C—C\equiv C\phi$ | and | $\phi C\equiv C—CH=CH\phi$ |
|---|---|---|
| Model A | | Model B | were prepared and subjected to cure conditions (Technical Report AFML-TR-76-71 June 1976). Model compound A, the Glaser coupling, produces 100% polymers. Model compound B, the Straus coupling, also produces polymers along with small amounts of phenyl naphthalene. These and DSC analysis indicate that the crosslinking reaction of the terminal acetylene group is much more complex than originally assumed and apparently proceeds by a number of simultaneously mechanistic routes. Thus, if the polyimide contains terminal C≡CH groups, and in the cure reaction there is produced Glaser or Straus couplings in the cured products, sensitivity to oxygen at high temperatures is to be expected. Thermogravimetric analysis of a polymer derived from:

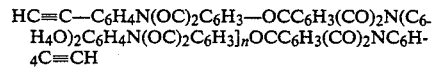

shows (Technical Report AFML-TR-75-30, July 1975, p. 61) that 75% of the sample weight is lost in the interval 560°+90° C. and that unusual behavior occurs above the region of the weight loss, indicating weight gain and that "the cause should be investigated".

Accordingly, it would appear to be a worthwhile technical objective to achieve the synthesis of polyimides which are devoid of terminal acetylenic structures, that is monoacetylene —CH≡CXH, but which still can undergo practical desirable acetylene-type chemistry to achieve the crosslinking of the polyimide. We have now discovered that this objective can be achieved by end-capping the polyimides with groups containing the vinylacetylene or enyne structure:

—CH=CH—C≡C— or interchangeably —C≡C—CH=CH—.

SUMMARY OF THE INVENTION

In accordance with the present invention, it has been found that insoluble, infusible polymerization products are readily obtained by polymerizing polyimides having terminal groups which contain conjugated vinylacetylene or enyne structures —CH=CH—C≡C— or —C≡C—CH=CH—.

The unsaturated crosslinkable polyimides of this invention have the formula (I):

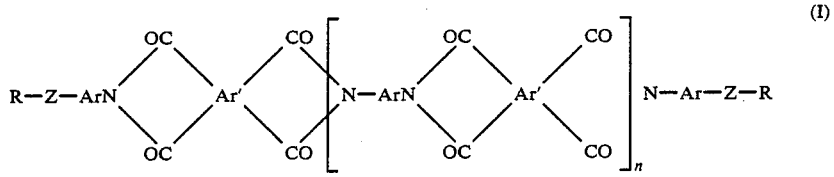

wherein:

Ar' is a tetravalent aromatic organic radical, the four carbonyl groups being attached directly to separate carbon atoms and each pair of carbonyl groups being attached to adjacent carbon atoms in Ar' radical except in the case of Ar' being a naphthalene radical, one or both pairs of the carbonyl groups may be attached to peri carbon atoms;

Ar is a divalent aromatic organic radical;

n is zero or an integer of 1 to 20, preferably 1 to 10;

R is hydrogen or an organic moiety containing 1 to 21 carbon atoms; and

Z is the structure —CH=CH—C≡C— or interchangeably —C≡C—CH=CH—.

In the Z structure, the vinyl portions, —CH=CH—, can be considered as the head portion and the acetylene portion, —C≡C— as the tail portion and thus Z can be attached to —Ar— and —R in a head-to-head orientation, thus —ArCH=CH—C≡C—R or in a tail-to-head orientation, thus —Ar—C≡C—CH=CH—R. In addition, the structure —CH=CH—C≡C— isomerizes easily to —C≡C—CH=CH—,

—CH=CH—C≡C—⇌—C≡C—CH=CH—.

In this invention, the term vinylacetylene or enyne, when shown as —CH=CH—C≡C— is meant to include the structure —C≡C—CH=CH— as its equivalent.

When n is zero in Formula I, the polyimide is the monomer of the structure (II):

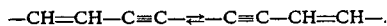
R—Z—ArN(OC\Ar'/CO)(CO/Ar'\OC)N—Ar—Z—R  (II)

When n is greater than zero, n may be identified as n''.

The polyimides (I) are concurrently prepared by amidation and imidation of the anhydride terminated compounds of the formula (III):

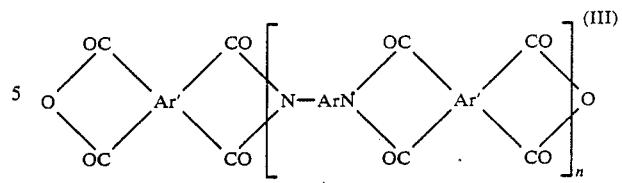

wherein n, Ar and Ar' have the same meaning as in (I), thus when n=0, III reduces to:

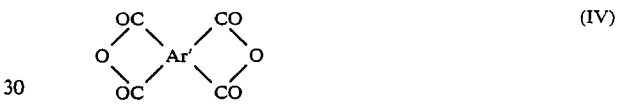

Amidation of (III) is accomplished by reaction (Eq. 1) with a monoamine $H_2N—Ar—ZR$, wherein Ar, Z and R have the same meaning as in I, the amidation occurs in the terminal anhydride group first with the formation of a terminal hemi-amic acid (V), thus:

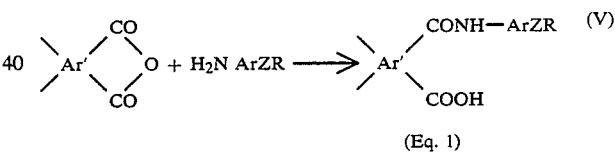

(Eq. 1)

which, on dehydration, has ring closure to give the imide structure (VI):

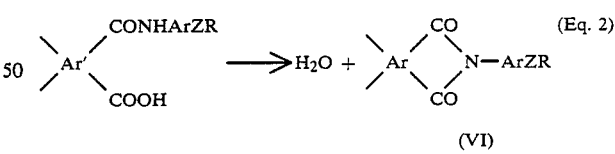

(Eq. 2)

Also, the imides of this invention can be prepared by amidating the amine-terminated polyimide oligomers of the formula VII:

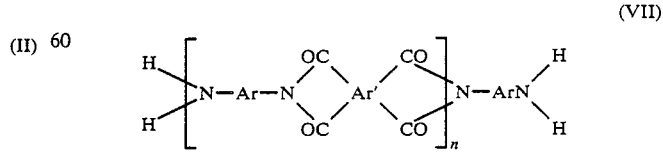

wherein n, Ar and Ar' have the same meaning as in Formula (1) with an unsymmetrical aromatic dianhydride monoimide of the formula (VIII):

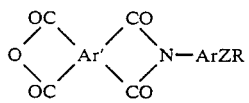

(VIII)

wherein Ar, Ar', Z and R have the same meaning as in Formula (I), thus

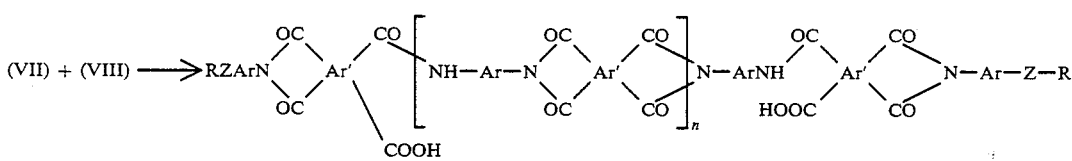

which is dehydrated (Eq. 4) to the imide (X)

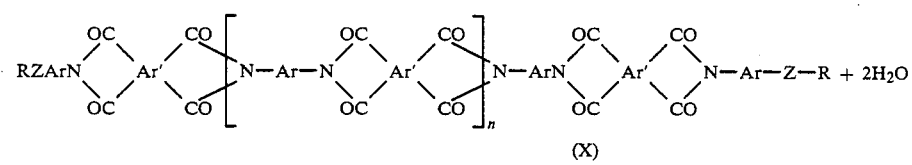

(Eq. 4)

The dehydration of the hemi-amic acids shown in Equations 2 and 4 can be achieved thermally or by chemical dehydration as, for example, by use of acid anhydrides, for example, acetic anhydride, propionic anhydride, or by azeotropic distillation as described in more detail hereinafter.

In the preparation of the enyne end-capped polyimides of this invention, tetra-esters or acid chlorides with a hydrohalide acceptor may be used instead of the dianhydrides. For preparing alcohol soluble oligomers, the dianhydride may be converted to an alcohol soluble hemi-ester by reaction with a lower aliphatic alcohol:

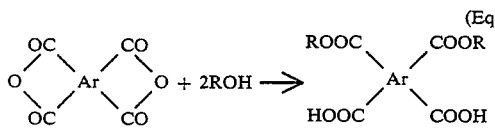 (Eq. 5)

which is reacted at a ratio of n+1 moles with n moles of $H_2NArNH_2$ and two moles of $H_2NArZ$—R and concentrated to a syrup which is useful as a laminating resin.

The amine-terminated oligomers (VII) used hereinabove as intermediates in the preparation of the polyimide (I) of this invention, as illustrated by Equation 3, are prepared by reacting a molar excess, i.e., n+1 moles of an aromatic diamine, $H_2NArNH_2$, with n moles of an aromatic dianhydride

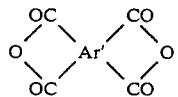

wherein Ar and Ar' have the same meaning as defined heretofore, and the aromatic diamine and the aromatic dianhydrides are the same pair of co-reactants used to prepare the anhydride-terminated oligomers represented by Formula III. The polyimide amine-terminated oligomers (VII) used as intermediates may be conveniently prepared by the same process used to synthesize the anhydride-terminated polyimides (III) used as intermediates for amidation except for the molar ratio of amine and anhydride used. These syntheses are exemplified in U.S. Pat. Nos. 3,897,395 and 4,058,505 and hereinafter with specific reference, for example, to the synthesis of the anhydride terminated polyimides.

The polyimide anhydrides (III) used in the above reactions in the synthesis of (I) of this invention are prepared by reacting a molar excess, i.e., n+1 moles of an aromatic dianhydride with n moles of an aromatic diamine. The aromatic dianhydride has the formula:

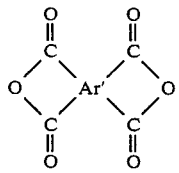

wherein Ar' is a tetravalent aromatic organic radical, preferably containing at least one ring of six carbon atoms, said ring characterized by benzenoid unsaturation, the four carbonyl groups being attached directly to separate carbon atoms and each pair of carbonyl groups being attached to adjacent carbon atoms in the Ar' radical except that when Ar' represents the naphthalene radical, one or both pairs of carbonyl groups may be attached to the peri carbon atoms.

The aromatic diamines useful in this preparation are represented by the formula $H_2N$—Ar—$NH_2$ wherein Ar is a divalent aromatic organic radical.

In preparing the anhydride-terminated polyimides, any of the aromatic tetracarboxylic acid dianhydrides known in the prior art can be used. Among the useful dianhydrides are 3,3',4,4'-benzophenonetetracarboxylic acid dianhydride, 1,4,5,6-tetracarboxylic dianhydride, 3,3',4,4'-diphenyl tetracarboxylic acid dianhydride, 1,2,5,6-naphthalene tetracarboxylic acid dianhydride, 2,2',3,3'-diphenyl tetracarboxylic acid dianhydride, 2,2-bis(3,4-dicarboxyphenyl) propane dianhydride, 3,4,9,10-perylene tetracarboxylic acid dianhydride, bis(3,4-dicarboxyphenyl) ether dianhydride, naphthalene-1,2,4,5-tetracarboxylic acid dianhydride, naphthalene-1,4,5,8-tetracarboxylic acid dianhydride, decahydronaphthalene-1,4,5,8-tetracarboxylic acid dianhydride, 4,8-dimethyl-1,2,3,5,6,7-hexahydronaphthalene-1,2,5,6-tetracarboxylic acid dianhydride, 2,6-dichloronaphthalene-1,4,5,8-tetracarboxylic acid dianhydride, 2,7-dichloronaphthalene-1,4,5,8-tetracarboxylic acid dianhydride, 2,3,6,7-tetrachloronaphthalene-1,4,5,8-tetracarboxylic acid dianhydride, phenanthrene-1,8,9,10-tetracarboxylic acid dianhydride, cyclopentane-1,2,3,4-tetracarboxyphenyl)propane dianhydride, 1,1-bis(2,3-dicarboxyphenyl)ethane dianhydride, 1,1-bis(3,4-dicarboxyphenyl)ethane dianhydride, bis(2,3-dicarboxyphenyl)methane dianhydride, bis(3,4-dicarboxyphenyl)methane dianhydride, bis(3,4-dicarboxyphenyl)sulfone dianhydride, and benzene-1,2,3,4-tetracarboxylic acid dianhydride. The first three mentioned dianhydrides are preferred.

Aromatic diamines useful in preparing the starting polyimides have the formula:

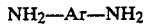

wherein Ar is a divalent aromatic organic radical. Preferred aromatic diamines are those wherein Ar is a divalent benzenoid radical selected from the group consisting of:

and multiples thereof connected to each other by $R^{III}$, e.g.,

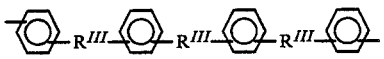

wherein $R^{III}$ is —CH=CH—,

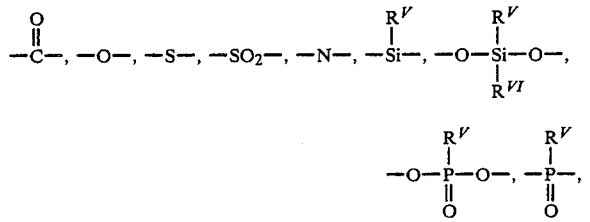

or an alkylene chain of 1-3 carbon atoms, wherein $R^V$ and $R^{VI}$ are each selected from the group consisting of alkyl and aryl containing one to six carbon atoms, e.g., methyl, ethyl, hexyl, n-butyl, i-butyl and phenyl. Preferred Ar' groups are:

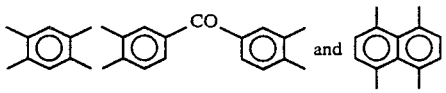

Examples of the aromatic diamines which are suitable for use in the present invention are 4,4'-diaminodiphenyl propane, 4,4'-diamino-diphenyl methane, benzidine, 3,3'-dichlorobenzidine, 4,4'-diamino-diphenyl sulfide, 3,3'-diamino-diphenyl sulfone, 4,4'-diamino-diphenyl ethyl phosphine oxide, 4,4'-diamino-diphenyl pehnyl phosphine oxide, 4,4'-diamino-diphenyl N-methyl amine, 4,4'-diamino-diphenyl N-phenyl amine and mixtures thereof, 3,3'-dimethyl-4,4'-diaminodiphenylmethane, 3,3'-diethyl-4,4'-diaminodiphenylmethane, 3,3'-dibromo-4,4'-diaminodiphenylmethane, 3,3'-dicarboxy-4,4'-diaminophenylmethane, 3,3'-dihydroxy-4,4'-diaminophenylmethane, 3,3'-disulpho-4,4'-diaminodiphenylmethane, 3,3'-dimethyl-4,4'-diaminodiphenylether, 3,3'-diethyl-4,4'-diaminodiphenylether, 3,3'-dimethoxy-4,4'-diaminodiphenylether, 3,3'-diethoxy-4,4'-diaminodiphenylether, 3,3'-dichloro-4,4'-diaminodiphenylether, 3,3'-dibromo-4,4'-diaminodiphenylether, 3,3'-dicarboxy-4,4'-diaminodiphenylether, 3,3'-dihydroxy-4,4'-diaminodiphenylether, 3,3'-disulfo-4,4'-diaminodiphenylether, 3,3'-dimethyl-4,4'-diaminodiphenylsulfide, 3,3'-diethyl-4,4'-diaminodiphenylsulfide, 3,3'-dimethoxy-4,4'-diaminodiphenylsulfide, 3,3-diethoxy-4,4'-diaminodiphenylsulfide, 3,3'-dichloro-4,4'-diaminodiphenylsulfide, 3,3'-dibromo-4,4'-diaminodiphenylsulfide, 3,3'-dicarboxyyl-4,4'-diaminodiphenylsulfide, 3,3'-dihydroxy-4,4'-diaminodiphenylsulfide, 3,3'-disulfo-4,4'-diaminodiphenylsulfide, 3,3'-dimethyl-4,4'-diaminodiphenylsulfone, 3,3'-diethoxy-4,4'-diaminodiphenylsulfone, 3,3'-dichloro-4,4'-diaminodiphenylsulfone, 3,3'-dicarboxy-4,4'-diaminodiphenylsulfone, 3,3'-dihydroxy-4,4'-diaminodiphenylsulfone, 3,3'-disulfo-4,4'-diaminodiphenylsulfone, 3,3'-diethyl-4,4'-diaminodiphenylpropane, 3,3'-dimethoxy-4,4'-diaminodiphenylpropane, 3,3'-dibromo-4,4'-diaminodiphenylPropane, 3,3'-dichloro-4,4'-diaminodiphenylpropane, 3,3'-dicarboxy-4,4'-diaminodiphenylpropane, 3,3'-dihydroxy-4,4'-diaminodiphenylpropane, 3,3'-disulfo-4,4'-diaminodiphenylpropane, 3,3'-dimethyl-4,4'-diaminobenzophenone, 3,3'-dimethoxy-4,4'-diaminobenzophenone, 3,3'-dichloro-4,4'-diaminobenzophenone, 3,3'-dibromo-4,4'-diaminobenzophenone, 3,3'-dicarboxy-4,4'-diaminobenzophenone, 3,3'-dihydroxy-4,4'-diaminobenzophenone, 3,3'-disulphodiaminobenzophenone, 3,3'-diaminodiphenylmethane, 3,3'-diaminodiphenylether, 3,3'-diaminodiphenylsulfide, 3,3'-diaminodiphenylsulfone, 3,3'-diaminodiphenylpropane, 3,3'-diaminobenzophenone, 2,4-diaminotoluene, 2,6-diaminotoluene, 1-isopropyl-2,4-phenylenediamine, 2,4-diaminoanisole, 2,4-diaminomonochlorobenzene, 2,4-diaminofluorobenzene, 2,4-diaminobenzoic acid, 2,4-diaminophenol and 2,4-diaminobenzenesulfonic acid and phenylene diamines. Preferred diamines are 4,4'-oxydianiline, 4,4'-sulfonyldianiline, 4,4'-methylene dianiline, 4,4'-diaminobenzophenone, 4,4'-diaminostilbene and the phenylene diamines, 2,4-diaminotoluene and all the meta and para isomers of $H_2NC_6H_4OC_6H_4OC_6H_4NH_2$.

The R groups may include any organic moiety that will not interfere with the functions of the polyimides as described herein. Preferably these groups are hydrocarbon or a multiplicity of hydrocarbon groups joined by ether, sulfite, ester and sulfonyl groups, such as —O—, —S—, —COO—, —OOC—, —S(O)$_2$—, etc.

Typical R groups suitable in the above formulas include: —CH$_3$, —C$_2$H$_5$, —C$_3$H$_7$, —C$_4$H$_9$, —C$_6$H$_{13}$, —C$_{10}$H$_{21}$, —C$_{18}$H$_{37}$, —C$_6$H$_{11}$, —C$_5$H$_9$, —C$_5$H$_8$CH$_3$, —C$_6$H$_{10}$C$_2$H$_5$, —CH$_2$C$_6$H$_{11}$, —CH$_2$CH$_2$C$_6$H$_{11}$, —C$_6$H$_5$, —C$_6$H$_4$CH$_3$, —C$_6$H$_4$C$_3$H$_7$, —C$_6$H$_3$(CH$_3$)$_2$, —C$_6$H$_9$OCH$_3$, —C$_6$H$_4$OC$_2$H$_5$, —C$_6$H$_4$OOCCH$_3$, —C$_6$H$_4$SO$_2$C$_6$H$_5$, —C$_6$H$_4$SO$_2$C$_6$H$_4$CH$_3$, —C$_6$H$_4$SO$_2$C$_6$H$_5$, —C$_6$H$_4$SO$_2$C$_{10}$H$_7$, —C$_6$H$_4$OC$_6$H$_5$, —C$_6$H$_4$OC$_6$H$_5$, —C$_6$H$_4$OCH$_3$, —C$_6$H$_4$OC$_2$H$_5$, —C$_6$H$_3$(CH$_3$)OC$_3$H$_7$, —C$_6$H$_4$OC$_6$H$_4$CH$_3$, —C$_{10}$H$_8$, —C$_{10}$H$_7$CH$_3$, —C$_{10}$H$_7$C$_2$H$_5$, —C$_{10}$H$_6$(CH$_3$)$_2$, —C$_{10}$H$_6$OCH$_3$, —C$_{10}$H$_6$OOCCH$_3$, —(C$_6$H$_4$)$_3$C$_3$H$_7$, —(C$_6$H$_4$)$_3$OC$_4$H$_9$, —(C$_6$H$_4$)$_3$OC$_6$H$_5$, —C$_6$H$_4$(OCH$_2$CH$_2$)$_2$H, —C$_6$H$_4$(OCH$_2$CH$_2$)$_3$H, —(C$_6$H$_4$O)$_3$C$_3$H$_7$, —CH$_2$CH$_2$(OCH$_2$CH$_2$)$_2$H, —CH$_2$CH$_2$(OCH$_2$CH$_2$)$_3$OOCCH$_3$, —CH$_2$CH$_2$OC$_6$H$_5$, —CH$_2$CH$_2$OOCCH$_3$, —CH$_2$CH(CH$_3$)OOCC$_6$H$_5$, —C$_6$H$_4$COOC$_2$H$_5$, —CH$_2$COOC$_6$H$_5$, etc.

The polyimide starting materials used in the process of this invention may be prepared conveniently as shown in U.S. Pat. Nos. 3,897,395 and 4,058,505 by reacting the dianhydride with the diamine in a phenol solvent of the formula:

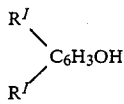

wherein each R$^I$ is hydrogen or a methyl radical, in the presence of certain organic azeotroping agents, particularly cyclic hydrocarbons of 6 to 8 carbon atoms and most preferably benzene or toluene, until most of the water of reaction is eliminated. The reaction temperature is less than 140° C. and also should be below the boiling point of the phenol used but higher than the boiling point of the azeotroping agent. The vapor phase temperature lies between that of the water azeotrope and no higher than 95° C. As the water of reaction and azeotroping agent are removed from the reaction mixture, quantities of the azeotroping agent are removed from the reaction mixture, quantities of the azeotroping agent are returned to the reaction mixture so as to maintain the temperature and reaction mixture volume substantially constant. It is preferred that the process is continuous with continuous removal of water and continuous return of azeotroping agent. This is conveniently done by the use of a conventional Dean-Stark trap and condenser wherein after the azeotrope condenses, the water preferably sinks to the bottom of the trap for subsequent removal and the azeotroping agent overflows the trap and returns to the reaction mixture. Initially, the trap is filled with azeotroping agent. For brevity, this apparatus will be referred to herein as cresol-benzene azeotropic apparatus.

By using an excess of the anhydride, the terminal groups of the polyimide will be anhydride groups. The more excess there is of the anhydride, the shorter will be the molecular length of the polyimide. Advantageously, the amount of excess anhydride is calculated in accordance with the desired length or molecular weight of the desired starting polyimide.

Similarly, by using an excess of the diamine, the terminal groups of the polyimides will be amine groups. The more excess there is of the diamine, the shorter will be the molecular length of the polyimide. Advantageously, the amount of excess diamine is calculated in accordance with the desired length or molecular weight of the desired starting polyimide.

It is apparent from an observation of compounds of the Formulas I to X and of Equations 1 to 4, that the polyimides of this invention are the reaction product of:

n moles of H$_2$NArNH$_2$,
N+1 moles of

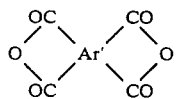

and
2 moles of H$_2$NArZ—R which can be reacted in stages as shown hereinabove, or can be reacted as a mixture in a single step or can react in a series of steps in a single reactor, particularly by using the azeotropic technique described above. For example, 2 moles of H$_2$NArZR can be reacted first with n+1 moles of

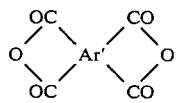

and thereafter n moles of H$_2$NArNH$_2$ added and the reaction completed in which the linkages formed can be either hemi-amic or imide; or n moles of H$_2$NArNH$_2$ are first reacted with n+1 moles of

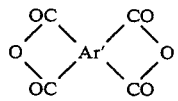

and thereafter 2 moles of H$_2$NArZ—R are added and the reaction completed.

A few illustrative examples of the monoamines, H$_2$NArZ—R which introduce the terminal NArZ—R moieties in the polyimides (I) of this invention are:

H$_2$NC$_6$H$_4$CH=CH—C≡CH
H$_2$NC$_6$H$_4$CH=CH—C≡CC$_6$H$_5$
o—H$_2$NC$_6$H$_4$OC$_6$H$_4$CH=CH—C≡CC$_6$H$_5$
m-H$_2$NC$_6$H$_4$OC$_6$H$_4$CH=CH—C≡CC$_6$H$_5$
p-H$_2$NC$_6$H$_4$OC$_6$H$_4$CH=CH—C≡CC$_6$H$_5$
H$_2$NC$_6$H$_4$SO$_2$C$_6$H$_4$CH=CH—C≡CC$_6$H$_5$
H$_2$NC$_5$H$_4$CH=CH—C≡C—C$_6$H$_4$OC$_6$H$_5$
H$_2$NC$_6$H$_4$CH=CH—C≡C—C$_6$H$_4$SO$_2$C$_6$H$_5$
H$_2$NC$_6$H$_4$OC$_6$H$_4$CH=CH—C≡C—C$_6$H$_4$SO$_2$C$_6$H$_5$
H$_2$NC$_6$H$_4$SO$_2$C$_6$H$_4$CH=CH—C≡CC$_6$H$_4$SO$_2$C$_6$H$_5$
H$_2$NC$_6$H$_4$SO$_2$C$_6$H$_4$CH=CH—C≡CC$_6$H$_4$OC$_6$H$_5$
H$_2$NC$_6$H$_4$OC$_6$H$_4$CH=CH—C≡C—C$_6$H$_4$OC$_6$H$_5$
H$_2$NC$_6$H$_4$CH=CH—C≡CC$_{18}$H$_{37}$
H$_2$NC$_6$H$_4$CH=CH—C≡C—C$_6$H$_4$C$_6$H$_4$C$_6$H$_5$
H$_2$NC$_6$H$_4$CH=CH—C≡C(C$_6$H$_4$)$_3$C$_3$H$_7$
H$_2$NC$_6$H$_4$CH=CH—C≡C(C$_6$H$_4$O)$_3$C$_3$H$_7$
H$_2$NC$_6$H$_4$CH=CH—C≡C—CH$_3$
H$_2$NC$_6$H$_4$OC$_6$H$_4$OC$_6$H$_4$CH=CH—C≡CC$_6$H$_5$

Compounds of the formula H$_2$NZR wherein Z is —CH=CH—C≡C—, are readily prepared by partial reduction by hydrogen of the precursor diacetylene compounds H$_2$NArC≡C—C≡CR by the procedure used by Straus for the conversion of C$_6$H$_5$C≡C—C≡CC$_6$H$_5$ to C$_6$H$_5$CH=CH—C≡C—C$_6$H$_5$ (Acetylene Homologues et Derives, by Pierre Piganiol, Dunod Publisher 1945, Paris, pp. 138–139). In the diacetylenes, which are not symmetrical such as in H$_2$NC$_6$H$_4$C≡C—C≡CC$_6$H$_5$, reduction in many cases yield two vinyl acetylenes, thus:

H$_2$NC$_6$H$_4$CH=CH—C≡CC$_6$H$_5$ and

H$_2$NC$_6$H$_4$C≡C—CH=CHC$_6$H$_5$ which for the purposes and objectives of this invention are equivalent.

The vinyl acetylene aryl amines, H$_2$NArZH, are also conveniently prepared by using the procedure of U.S.

Pat. No. 4,162,265 which uses $NH_2ArC\equiv CH$ as the starting material, then protects the amino group, e.g., by conversion to $CH_3CONHArC\equiv CH$, followed by coupling with the copper catalysis in an inert atmosphere to yield $CH_3CONHArCH=CH-C\equiv C-ArNHOCCH_3$. Partial hydrolysis yields $CH_3CONHArCH=CH-C\equiv CArNH_2$ and $H_2NArCH=CHC\equiv CArNHOCCH_3$. Then diazotization and treatment with alcohol yields $CH_3CONHArCH=CH-C\equiv ArH$ and $CH_3CONHArC\equiv C-CH=CHArH$. Further hydrolysis yields the isomeric $H_2NArCH=CH-C\equiv CArH$ and $H_2NArC\equiv CCH=CHArH$. The amino aryl diacetylene compounds which can be reduced by partial hydrogenation to the corresponding vinyl acetylene compounds as shown hereinabove, are prepared by well known chemical reactions which involve coupling of monoacetylenic compounds having terminal $-C\equiv CH$ or $-C\equiv CX$ functions wherein X is a halogen such as iodine, bromine or chlorine.

Ref. 1. Acetylenic Compounds in Organic Synthesis, by R. A. Raphael, Butterworths Scientific Publications, 1955, London; and Ref. 2. Acetylene Homologues et Derives, by Pierre Piganiol, Dunod 1945, Paris.

One method involves converting the 1-haloacetylene to a Grignard derivative, $R^VC\equiv C-MgX$, and reacting it with the 1-halogeno-acetylene $R^{VI}C\equiv CX$ thus,

Ref. 3. Liebigs, Ann 572, 116 (1951)
Ref. 4. I J. Chem. Soc. (1954) 1704
where $R^V$ and $R^{VI}$ represent moieties having carbon atoms attached to the $-C\equiv C-$ function and, in some cases, hydrogen. Instead of the Grignard reagents, an alkali acetylide, such as sodium, potassium or lithium acetylide can be used, thus:

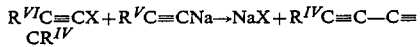

(See R. A. Raphael in Ref. 1, p. 16, and Bull. Soc. Chem. 53, 1533–1537 (1933), and J. Chem. Soc. (1945) 1009.

Also, the diacetylenes undergo similar reaction and can be converted to the 1-halogenoacetylide or alkali acetylides, thus,

(See J. Chem. Soc., p. 44 (1951), p. 1933 (1952) and Chem. Ber. 84, 545 (1951).)

The nitroaryl acetylenes, $O_2NArC\equiv CH$ can be subjected to coupling to give:

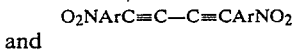
and

which on reduction of the nitro groups, yield the amines:

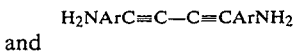
and

These diamines and monoamines are new chemical compounds.

When $H_2NArC\equiv CH$ is used in a coupling reaction, the $H_2N$ group must first be blocked so that it will not interfere with the coupling reaction, as for example, to an amide or imide function such as the acetamide, toluenesulfonamide or the phthalimide, thus,

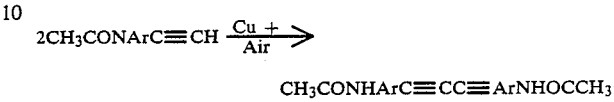

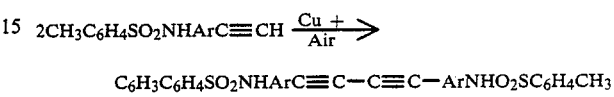

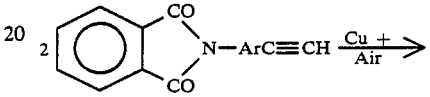

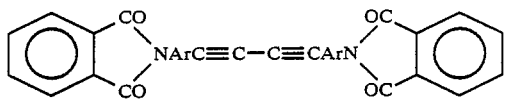

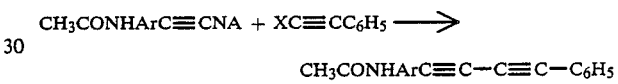

These compounds having one or two cyclic imide terminal groups are very useful, including the corresponding naphthalene ortho and peri compounds. Hydrolysis with alcoholic or aqueous sodium hydroxide liberates the free amide to give, e.g., $H_2NArC\equiv C-C\equiv CArNH_2$ from the first three equations, and $H_2NArC\equiv C-C\equiv CC_6H_5$ from the fourth equation. This procedure of coupling amide derivatives of acetylenic compounds is illustrated in U.S. Pat. No. 4,162,625 where the coupling is performed in an inert atmosphere to produce vinyl acetylene derivatives, $-C\equiv C-CH=CH-$. The same procedure when performed in an oxygen atmosphere produces diacetylene $-C\equiv C-C\equiv C-$.

Conjugated diacetylene can also be prepared by the so-called oxidative coupling of monoacetylenes having a terminal $-C\equiv CH$ function, thus

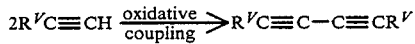

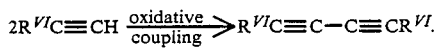

One procedure involves mixing the ethynyl compound with an aqueous solution of cuprous chloride in an atmosphere of oxygen. Acetylenes of widely varying structural types have been prepared by this method (Reference 1, p. 127). The use of two different acetylenic components in the coupling reaction produces some cross-coupling and the expected three-di-acetylenes are obtained, such as the two symmetrical diacetylenes shown above and the unsymmetrical product $R^VC\equiv C-C\equiv CR^{VI}$. These products are readily separated on the basis of size and the type of substituents $R^V$ and $R^{VI}$ (Reference 1, p. 128). Sometimes the mono-acetylene is converted to the copper derivative and the copper compounds subjected to coupling in the presence of air (oxygen). For the amines of the formula $H_2N-Z-R$ used in the practice of this invention, the amine aryl acetylenes $H_2NArC\equiv CH$ are satisfactory intermediates for conversion to the diacetylene and the vinylacetylene compounds. These $NH_2ArC\equiv CH$ compounds are readily obtained by reacting $O_2NArCOCH_3$ with $PCl_5$ or oxalyl chloride in dimethylformamide followed by treatment with alkali to give $O_2NArC\equiv CH$. The $NO_2$ group is easily reduced by sodium dithionate. Alternatively, the $NO_2$ group can be left unreduced until coupling is completed and then the $NO_2$ group reduced to $-NH_2$.

The diamino-diacetylenes are useful intermediates for preparing the mono-amino compounds by first protecting one amino group by amide formations and thereafter converting the remaining amino group to a diazonium salt followed by reacting with ethyl alcohol to eliminate $N_2$ yielding the hydrocarbon functions, thus when J represents $CH_3CO-$ or $CH_3C_6H_4SO_2-$ and Q is

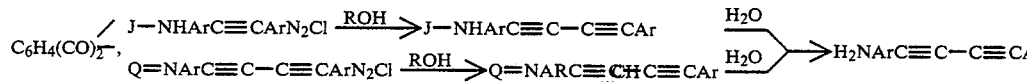

Cross-coupling (oxidative coupling) of an amide of the aminoaryl acetylene, $J-NHArC\equiv CH$ or $Q=NArC\equiv CH$ with a different acetylene compound free of amide or amine group, $RC\equiv CH$, produces the unsymmetrical cross-coupled product, $J-NHArC\equiv C-C\equiv CR$ or $Q=NArC\equiv C-C\equiv CR$, which on hydrolysis give $H_2NArC\equiv C-C\equiv CR$ as well as the two symmetrical products, one of which, as shown above, on hydrolysis gives the diamino derivative $H_2NArC\equiv C-C\equiv CArNH_2$ useful per se as a diamine in polyamide and polyimide syntheses as well as the symmetrical $RC\equiv C-C\equiv CR$ which is free of amino-groups. This latter compound is useful as a chemical intermediate and can also function as a "dieneophile" and as a di-yne. It can function as Diels-Alder donor compound and function as a coreactive plasticizer for all types of polymers containing terminal or pendant $CH_2=CH-$, $CH_2=C<$, $-CH=CH-$, $-C\equiv CR$ groups.

The nature of the reactivity of the terminal $-CH=CH-C\equiv C-$ structures in the polyimides of this invention differs substantially from polyimide compounds having a terminal monoacetylenic structure $-C\equiv C-$.

The 1,3 enyne character of $-CH=CH-C\equiv C-$ qualifies it as a donor type of molecule in the Diels-Alder type reaction so that it is capable of undergoing a 1,4 addition reaction with olefinic unsaturated compounds known as dienophiles, such as those containing $CH_2=C$, $-CH=CH-$, and $-C\equiv C-$ structures. The dienophile is activated by electro withdrawn substituents such as $-COOR$, $-CN$, $-C_6H_5$, $-CONR_2$, $-SO_2$, etc. (Reference: Organic Chemistry, Cram and Hammond, McGraw-Hill Publisher, New York, 1959; also Organic Chemistry, Fieser and Fieser, Reinhold Publishing Company, New York, 1961, p. 206-11). Typical examples of the Diels-Alder reaction are the reaction of butadiene and maleic anhydride to give 1,2,3,6-tetrahydrophthalic anhydride, thus:

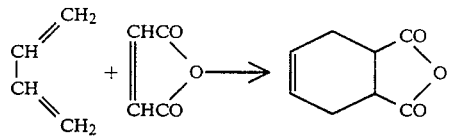

and the related reactions with an acetylene dicarboxylate to give a 1,2,3,6-dihydrophthalate diester, thus,

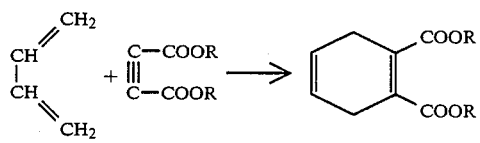

or the reaction of diacetylene with maleic anhydride to give phthalic anhydrides, thus,

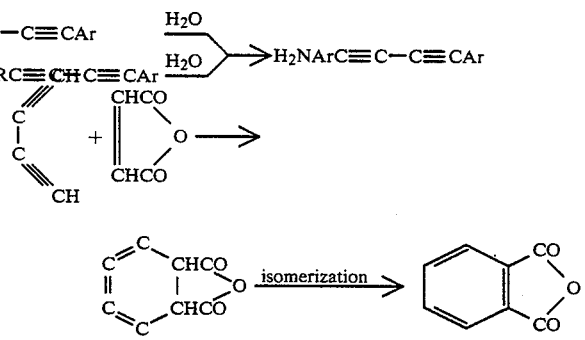

Furthermore, the enyne compounds of this invention can function as the "dienophile" in a Diels-Alder reaction either with another Diels-Alder donor, e.g., a compound containing butadiene, $-CH=CH-CH=C-$ structure, or with itself as a compound containing an enyne $-CH=CH-C\equiv C-$ structure. Thus a vinylacetylene structure, $-CH=CH-C\equiv C-$ can function both as a "diene" or as a "dienophile" or as both, in reactions which offer another route to benzenoid derivatives. (See Ref. 1 above, p. 160—VSW and for Comprehensive Reviews see H. L. Holmes, Organic Reactions 4, 60 (1948) and K. Alder, New Methods of Preparative Organic Chemistry, New York, 1948, p. 381 VSW). In contrast, a compound having a single $-CA\equiv C-$ structure, can function only as the dienophile and not as a donor in the Diels-Alder type reaction.

Accordingly, it has been discovered that the polyimides of this invention are capable of undergoing this Diels-Alder type of reaction with a large variety of dienophiles whether they are monomeric, oligomeric or polymeric, or whether they are monofunctional or polyfunctional, e.g., difunctional, trifunctional, etc. The polyfunctional dienophiles chain extend and crosslink the polyimides of this invention. Such addition products can be viewed in a broad sense as copolymers. However, they differ from the accepted type of copolymer which is obtained by chain formation with the opening of a double or triple bond, whereas in the Diels-Alder reaction there occurs the formation of six-membered rings.

A large number of dienophiles are available for the 1,4-cycloaddition to the polyimides of this invention. One particularly useful class is the class of maleimide end-capped polyimides having the formula:

$$\text{(XI)} \quad \begin{array}{c} CH-CO \\ \parallel \\ CH-CO \end{array} N-\left[ArN\begin{array}{c}OC\\ \diagdown \\ OC\end{array}\begin{array}{c}CO\\ \diagup \\ CO\end{array}Ar'\begin{array}{c}\diagdown \\ \diagup\end{array}N\right]_{n'}-ArN\begin{array}{c}OC-CH\\ \parallel \\ OC-CH\end{array}$$

wherein Ar and Ar' are the same as those given in formula (I) herein above and n' is equal to n of formula (I). The syntheses of a number of maleimides illustrative of XI are given in U.S. Pat. No. 3,929,713, Dec. 30, 1975.

Another useful class is that having the formula:

$$\text{(XII)} \quad CH_2=CH-R'-N\begin{array}{c}OC\\ \diagdown \\ OC\end{array}\begin{array}{c}CO\\ \diagup \\ CO\end{array}Ar'\begin{array}{c}\diagdown \\ \diagup\end{array}N-\left[ArN\begin{array}{c}OC\\ \diagdown \\ OC\end{array}\begin{array}{c}CO\\ \diagup \\ CO\end{array}Ar'\begin{array}{c}\diagdown \\ \diagup\end{array}N\right]_{n'}-R'-CH=CH_2$$

wherein Ar' and Ar have the same meaning as in Formula I and R' is an organic moiety containing 1 to 12 carbon atoms, and n' has the same meaning as n. The preferred examples of R' are —CH$_2$— and —C$_6$H$_4$—. The syntheses of a number of polyimides, illustrative of XII, are given in U.S. Pat. No. 3,897,395, July 29, 1975.

A third useful class of polyimides that can function as dienophiles is given by the formula:

$$R°C\equiv C-R'-N\begin{array}{c}OC\\ \diagdown \\ OC\end{array}\begin{array}{c}CO\\ \diagup \\ CO\end{array}Ar'\begin{array}{c}\diagdown \\ \diagup\end{array}N-\left[ArN\begin{array}{c}OC\\ \diagdown \\ OC\end{array}\begin{array}{c}CO\\ \diagup \\ CO\end{array}Ar'\begin{array}{c}\diagdown \\ \diagup\end{array}N\right]_{n'}-R'-C\equiv CR°$$

wherein n' has the same meaning as n, and Ar', Ar and n have the same meaning as in Formula I, R' is the same as in Formula XII, i.e. a divalent organic moiety containing 1 to 12 carbon atoms. R° is H or R wherein R has the same meaning as in Formula I. The preferred examples of R' are —CH$_2$— and —C$_6$H$_4$— and the preferred examples of R° are H, —C$_6$H$_5$ and —C$_6$H$_4$—O—C$_6$H$_5$. The synthesis of dienophile polyimides of this type is described in U.S. Pat. Nos. 3,987,395 and 3,845,018.

A still further useful class of polyimides that function as dienophiles is that given by the formula:

$$R'''\begin{array}{c}CO\\ \diagdown \\ CO\end{array}N-\left[ArN\begin{array}{c}OC\\ \diagdown \\ OC\end{array}\begin{array}{c}CO\\ \diagup \\ CO\end{array}Ar'\begin{array}{c}\diagdown \\ \diagup\end{array}N\right]_{n'}-ArN\begin{array}{c}OC\\ \diagdown \\ OC\end{array}R'''$$

wherein n' has the same meaning as n, and Ar, Ar' and n are the same as given in Formula I, and R''' represents RA°C≡CAr<, R°CH=CHAr<, e.g., C$_6$H$_5$≡CC$_6$H$_3$<, H$_2$C=CHC$_6$H$_3$<, HC≡CC$_6$H$_4$OC$_6$H$_3$<, C$_6$H$_5$OC$_6$H$_4$C≡CC$_6$H$_3$<, CH$_3$C≡CC$_6$H$_4$C$_6$H$_3$<, H$_2$C=CHC$_6$H$_3$<, HC≡CC$_6$H$_4$OC$_6$H$_3$<, C$_6$H$_5$OC$_6$H$_4$C≡CC$_6$H$_3$<, CH$_3$C≡CC$_6$H$_4$C$_6$H$_3$<, C$_3$H$_7$C≡CC$_6$H$_3$<, C$_6$H$_5$SO$_2$C$_6$H$_4$C≡CC$_6$H$_3$<, CH$_3$C$_6$H$_4$CH=CHC$_6$H$_3$<, C$_6$H$_4$OC$_6$H$_4$CH=CHC$_6$H$_3$<, H(CH$_2$CH$_2$O)$_2$— CH$_2$CH$_2$CH=CHC$_6$H$_3$<, etc. wherein R° is the same as defined for R.

Some polyimides of this class are disclosed in U.S. Pat. No. 4,075,171.

Other CH$_2$=C<, —HC=CH—, —C≡C—, and CH≡C— terminated polyimides useful as dienophiles in the practice of this invention are given in U.S. Pat. Nos. 4,166,168; 4,168,360; 4,168,366; 4,168,367 and 3,998,786.

It is also to be noted that since many simple monomers contain such groups as CH$_2$=C<, HC≡C—, —C≡C— or >C=C<, they can function either as comonomers or as dienophiles for addition reaction with the new polyimides of this invention. For purposes of this invention such monomers may be classified as having RCH=C(R°)— or RC≡C— groups wherein R and R° are as defined above (representing either hydrogen or an organic moiety having 1-20 carbon atoms).

Some typical monomers are the maleyl compounds such as maleic anhydride $$\begin{array}{c}CH-CO\\ \parallel \quad \diagdown \\ \quad \quad \quad O,\\ \diagup \\ CH-CO\end{array}$$

and its esters, $$\begin{array}{c}CHCOOR^{IV}\\ \parallel \\ CHCOOR^{IV}\end{array}$$

wherein R$^{IV}$ is an organic moiety containing 1 to 21 carbon atoms; the maleimides such as $$\begin{array}{c}CHCO\\ \parallel \quad \diagdown \\ \quad \quad \quad NR^{IV};\\ \diagup \\ CHCO\end{array}$$

the acetylenic carboxylic esters, R$^{IV}$C≡C—COOR$^{IV}$; R$^{IV}$OOCC≡C—COOR$^{IV}$; the dimaleimides $$\begin{array}{c}CHCO\\ \parallel \quad \diagdown \\ \quad \quad \quad N-Ar-N\\ \diagup \\ CHCO\end{array}\begin{array}{c}OCCH\\ \diagup \quad \parallel \\ \\ \diagdown \\ OCCH\end{array}$$

wherein Ar is as defined in Formula (I); and the end-capped polyimides selected from the class of oligomers and polymers derived from the reaction of n moles of Ar(NH₂)₂, n+1 mole of Ar(CO)₂O and 2 moles of a monoaryl amine having mono —CH=CH— or mono —C≡C— unsaturation as well as the monomers of this reaction when n equals zero.

Some other illustrative examples are styrene, the divinyl benzenes, the diethynyl benzenes, methyl methacrylate, glycoldimethacrylate, allylmethacrylate, acrylamide, ethylenediamine dimethacrylamide, acrylonitrile, maleic anhydride, diethyl maleate, diallyl fumarate, dipropargyl phthalate, dibutyl itacomate, a poly(ethylene-maleate), a poly(ethylenefumarate), 4,4'-diethynyl diphenyloxide, diphenyl maleate, N-phenyl maleimide, N-(vinyl phenyl)maleimide, N-(ethynylphenyl)maleimide, dipropargyl maleate, diallyl maleate, the acetylenic esters such as HC≡CH-COOCH₂CH=CH₂, C₆H₅C≡C—COOCH₂CH=CH₂, C₆H₅C≡COOCH₂C≡CH, HC≡C—C₆H₄OOCC≡CCOOC₆H₄C≡CH, H₂C=CHC₆H₄OOCC≡C—COOC₆H₄CH=CH₂, etc. In the vinylidene (CH₂=C<) monomers, one valence bond is preferably attached to hydrogen to give a vinyl monomer. However this bond may also be attached to various other groups such as hydrocarbyl groups of 1-20 carbon atoms, including alkyl aryl, cycloalkyl, alkenyl, etc., halogen, cyano (CN), OR, OOCR, CONR₂, COOR, etc. Other typical compounds are methyl alpha-chloroacrylate, methyl alpha-cyanoacrylate, alpha-methylstyrene, alpha-ethylstyrene, alpha-phenylstyrene, methacrylonitrile, dimethyl methylenemalonate, diethyl itaconate, vinyl benzoate, isopropanyl acetate, dimethylacrylamide, etc.

The Diels-Alder addition product usually is formed by the equimolar reaction of one donor function —CH=CH—C≡C— with one dienophile function, e.g., one CH₂=CH—, or one —C≡C—, or one

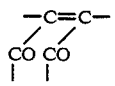

function. Thus two donor functions react with two dienophile functions. However, since the donor polyimides of this invention, and the dienophile acceptors are capable of homopolymerization, mixture in which either the donor or acceptor functions are in a minor or in a very large excess, completely polymerize by Diels-Alder addition together with the normal double and triple bond polymerization. These polymerizations occur by simply heating the mixture of reactants.

The products of this invention can be converted to the insoluble, infusible state by heat alone, such as by heating at temperatures in the range of 180° C. to 380° C., or even at lower temperatures, such as 100° C. or 200° C. or, if desired, by the addition of catalysts that generate free radicals such as benzoyl peroxide, the perbenzoates, cumyl mono and diperoxides, and a host of others that are well known in the vinyl monomer art, which include redox systems which promote polymerization of CH≡C— containing monomers at or even below room temperature, or by ionizing radiation or ultraviolet radiation, etc.

In many cases it may also be desirable to post-cure the products within the same ranges of temperatures or even higher temperatures, e.g. up to 425° C.

These products can be compounded with fillers of all sorts in the preparation of molding compounds, such as with graphite and quartz fibers or fillers to maintain high temperature resistance, etc.

The products of this invention are particularly useful as coatings and bonding agents for metals such as iron, copper, aluminum, steel, etc., either alone or as mixtures with other compounds containing two to four terminal CH₂=C<, CH≡C—, or

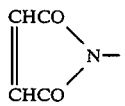

structures.

The new polyimides of this invention can be used as varnishes and coatings in appropriate solvents which depend on the nature of the constituent diamine and dianhydrides used in the synthesis of the polyimide esters.

In most cases the solvent is an aprotic organic compound having a dielectric constant between 35 and 45, preferably one which is water-soluble. Representative aprotic compounds are N,N-dimethylformamide, N,N-diethylformamide, N,N-dimethylmethoxyacetamide, N-methyl caprolactam, caprolactam, N,N-dimethylacetamide, N,N-diethylacetamide, dimethyl sulfoxide, N-methyl-α-pyrrolidone, tetramethylurea, hexamethylphosphonamide, tetramethylene sulfone, N,N,N',N'-tetramethylethylmalonamide, N,N,N',N'-tetramethylglutaramide, N,N,N',N'-tetramethylsuccinamide, thiobis(N,N-dimethylacetamide), bis(N,N-dimethylcarbamylmethyl)ether, N,N,N'N'-tetramethylfuraramide, methylsuccinonitrile, N,N-dimethylcyanocetamide, N,N-dimethyl-β-cyano-propionamide, N-formyl-piperdine and butyrolactone, etc.

Of the solvents, dimethylacetamide is most preferred. Other preferred solvents are dimethylformamide, N-methyl pyrrolidone, dimethyl sulfoxide, butyrolactone and caprolactate.

In many cases, non-aprotic solvents may also be used. For example, xylene, phenol, anisole, benzonitrile, acetophenone, methylphenylether, methylene chloride, chloroform, carbon tetrachloride or mixtures of these with each other, with the aprotic solvents or with relatively poor solvents such as benzene, toluene, cyclohexane, cyclohexene, dioxane, butyl cellosolve and the like.

SPECIFIC EMBODIMENTS OF THE INVENTION

The invention is illustrated by the following examples which are intended merely for purposes of illustration and are not to be regarded as limiting the scope of the invention or the manner in which it may be practiced. Unless specifically indicated otherwise, parts and percentages are given by weight.

EXAMPLE I

Preparation of Anhydride-Terminated Oligomeric Polyimide #1

Into a 100 ml. three-neck, round bottom flask equipped with a magnetic stirrer, thermometer, condenser, gas inlet tube, dropping funnel, etc. there is placed, under nitrogen atmosphere, a solution of benzophenonetetracarboxylic acid anhydride (BTCA) (6.444 g., 0.02 mole) in 25 ml. of dimethylacetamide (DMAC). Then a solution of 4,4'-oxydianiline (ODA) (2.00 g., 0.01 mole) in 15 ml. of DMAC is added over a period of 15 minutes. The reaction, which is exothermic, is maintained at 40° C. during the addition, following which it $$H_5C_6C{\equiv}C-CH{=}CHC_6H_4N\begin{smallmatrix}OC\\ \diagup\\ \diagdown\\ OC\end{smallmatrix}C_6H_3COC_6H_3(CO)_2NC_6H_4O-C_6H_4N(QC)_2C_6H_3COC_6H_3\begin{smallmatrix}CO\\ \diagup\\ \diagdown\\ CO\end{smallmatrix}N-C_6H_4CH{=}CH-C{\equiv}CC_6H_5$$

POLYIMIDE #1 is heated at 85°–90° C. for 15 minutes. To this clear amber-colored solution, acetic anhydride (3.60 g., 0.03 mole) is added and the mixture is heated to 125° C. Within 15 minutes a yellow precipitate is formed. After heating the reaction mixture for one hour, the solvents are removed in a rotary flash evaporator. The residual light-yellow solid is washed with anhydrous ether and dried in a vacuum oven at 140° C. to afford a quantitative yield. It softens slightly on a Fisher-Johns melting point apparatus at 120° C. and does not melt when heated to 300° C. The product is soluble in m-cresol and N-methyl-2-pyrrolidone and only slightly soluble in boiling benzonitrile, acetophenone or DMAC. The elemental analysis is found to be for C: 68.3% and for H: 2.4%, which is in good agreement with the calculated values for $C_{46}H_{20}N_2O_{13}$ having the formula:

$O(OC)_2C_6H_3COC_6H_3(CO)_2NC_6H_4OC_6H_4-$
$N(OC)_2C_6H_3COC_6H_3(CO)_2O$

EXAMPLE II

Preparation of Hemi-Amide of Polyimide of Example I

Into the reaction equipment used in Example I there is placed 50 ml. of N-methyl-2-pyrrolidone, 4.04 gm. of polyimide #1, 2.17 gm. of m-$H_2NC_6H_4CH{=}CH-C{\equiv}CC_6H_5$ and the mixture is heated at 100° C. for 10 minutes or until a clear solution is obtained. Water:methanol is added to the precipitate and washes the product which is isolated by filtration and dried in a vacuum oven at 110°–120° C. to give an almost quantitative yield of 6.0 g. The elemental analysis of 75.26% carbon and 3.36% hydrogen are in good agreement with the calculated values for $C_{78}H_{42}N_4O_{13}$ having the formula:

$$H_5C_6C{\equiv}C-CH{=}CH_6H_4NH\begin{smallmatrix}O\\ \|\\ \diagdown\end{smallmatrix}\\ \begin{smallmatrix}C\\ \diagup\\ HOOC\end{smallmatrix}-C_6H_3COC_6H_3(CO)_2NC_6H_4O-C_6H_4N(OC)_2C_6H_3COC_6H_3\begin{smallmatrix}CONHC_6H_4CH{=}CH-C{\equiv}C-C_6H_5\\ \diagup\\ \diagdown\\ COOH\end{smallmatrix}$$

(Amic-Acid #1)

EXAMPLE III

Cyclization of Hemi-Amide of Example II

Using the m-cresol-benzene technique, there is allowed to react at reflux 6.0 g. of the hemi-amid of Example II in 40 ml. of m-cresol and 10 ml. of benzene until no more water is collected in the Dean-Stark trap. The benzene is removed by distillation and methanol:water is added to the reaction flask and the precipitate is removed by filtration and dried in a vacuum oven at 70°–80° C. There is obtained 5.47 g. of the cyclized product. The elemental analysis of 77.55% C and 3.10% N are in good agreement with the calculated values for $C_{78}H_{38}N_4O_{11}$ having the formula:

When heated at 260° C. on a Fisher-Johns melting point apparatus, the polyimide becomes insoluble and infusible.

EXAMPLE IV

Preparation of Anhydride-Terminated Polyimide #1

Using the m-cresol benzene azeotropic procedure, there is allowed to react benzophenone-tetracarboxylic acid anhydride (BTCA) (4.0279 g., 0.0125 mole) and 1,3-di(3-aminophenoxy)-benzene (DAPB-3,3) (2.9223 g., 0.01 mole) in 40 ml. of m-cresol and 10 ml. of benzene. There is obtained 5.7 g. of polyimide #2 which is a light yellow powder, soluble in m-cresol, DMAC, sulfolane and dioxane. In a Fisher-Johns melting point apparatus, this melts at 200° C. The TGA in air shows losses of 1% at 200° C., 3% at 300° C., 4% at 400° C., 5% at 500° C. and 17% at 600° C. The elemental analysis is C: 71.4% and H: 3.2%, which are in excellent agreement with the calculated values of $C_{157}H_{80}N_8O_{35}$ for the formula:

$O(OC)_2C_6H_3COC_6H_3(CO)_2[NC_6H_4OC_6H_4OC_6H_4-$
$N(OC)_2C_6H_3COC_6H_3(CO)_2]_4O$

EXAMPLE V

Preparation of Imide of Anhydride-Terminated Polymer #2

In the same equipment used in Example III, there is added 5.2 g. of polyimide #2, 40 ml. of m-cresol, and 1.1 g. of $H_2NC_6H_4C{\equiv}C-CH{=}CH-C_6H_5$ and the mixture is heated at reflux until no more water is collected in the Dean-Stark trap. The elemental analysis is found to show C: 75.43% and H: 3.19%, which values are in good agreement with the calculated values for $C_{189}H_{96}N_{10}O_{33}$ having the formula:

$C_6H_5C{\equiv}C-CH{=}CHC_6H_4-N(OC)_2C_6H_3COC_6H_3(CO)_2[NC_6H_4OC_6H_4N(OC)_2-$
$-C_6H_3OCO_6H_3(CO)_2]_4N-C_6H_4C{\equiv}C-CH{=}CH-C_6H_5$

POLYIMIDE #2

EXAMPLE VI

There is added 4.0279 g. of BTCA to a mixture of 40 ml. of m-cresol and 10 ml. of benzene in the flask of a continuous azeotroping apparatus. The Dean-Stark trap is filled with benzene, then there is added 0.808 g. of $H_2N-C_6H_4CH{=}CH-C{\equiv}C-C_6H_5$ to the reaction mixture. The reaction mixture is heated at reflux for 15 minutes. Then there is added 2.9223 g. of DAPB-3,3'

EXAMPLE XI

Preparation of Anhydride-Terminated Oligomeric Polyimide #6

Using the same azeotropic techniques as shown, BTCA and 2,4-diaminotoluene (DAT) are reacted in a molar ratio of 6 to 5 to obtain polyimide #6 whose elemental analysis conforms with the formula:

$$O(OC)_2C_6H_3COC_6H_3(CO)_2[NC_6H_3(CH_3)N(OC)_2C_6H_3COC_6H_3(CO)_2]_5O$$

EXAMPLE XII

Preparation of Anhydride-Terminated Oligomeric Polyimide #7

Replacement of the BTCA in Example X by an equivalent amount of pyromellitic dianhydride produces polyimide #7 which has the formula:

$$O(OC)_2C_6H_2(CO)_2[NC_6H_3(CH_3)N(OC)_2C_6H_2(CO)_2]_5O$$

EXAMPLE XIII

The anhydride-terminated polyimides #3, 4, 5, 6, and 7 are converted individually by the procedure of Example V to diacetylene-terminated polyimides by reaction with the three amines:
a. $NH_2C_6H_4CH{=}CH{-}CH{\equiv}CH$
b. $NH_2C_6H_4CH{=}CH{-}CH{\equiv}CCH_3$
c. $NH_2C_6H_4CH{=}CH{-}C{\equiv}CC_6H_5$ These are summarized in Table I:

| Polyimide # | Polyimide Anhydride Used | Aminoacetylene Used |
|---|---|---|
| 4 | #3 | a |
| 5 | #3 | b |
| 6 | #3 | c |
| 7 | #4 | a |
| 8 | #4 | b |
| 9 | #4 | c |
| 10 | #5 | a |
| 11 | #5 | b |
| 12 | #5 | c |
| 13 | #6 | a |
| 14 | #6 | b |
| 15 | #6 | c |
| 16 | #7 | a |
| 17 | #7 | b |
| 18 | #7 | c |

When heated alone, or with small amounts of dicumyl peroxide, each of these yield insoluble, infusible cross-linked polymers.

EXAMPLE XIV

A mixture of 30 parts of polyimide #3, 70 parts of long fibered asbestos and 0.25 parts of cumyl peroxide is blended thoroughly and preformed into a one-inch disc which is compression molded at 1000 pounds per square inch at 265° C. for 5 minutes to yield a hard insoluble, infusible, molded product.

Similarly, a glass fiber reinforced composite is prepared by impregnating 181 E Glass Fabric with a solution of polyimide #3 in N-methyl pyrrolidinone to a total resin content of about 35% and the solvent removed by drying. The laminate is formed by stacking four sheets of impregnated glass fabric and curing at 250° C. at 200 pounds per square inch. The laminate is then post cured at 280° C. for 12 hours and 300° C. for 12 hours and shows a flexural strength value of 52,600 psi.

EXAMPLE XV

Using published procedures as given above, the following polyimides containing terminal groups that can function as dienophiles (DIENO) for the vinylacetylenic donors of this invention are prepared and designated as DIENO polyimides #1 to 6, inclusive.

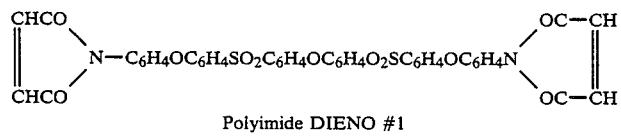

Polyimide DIENO #1

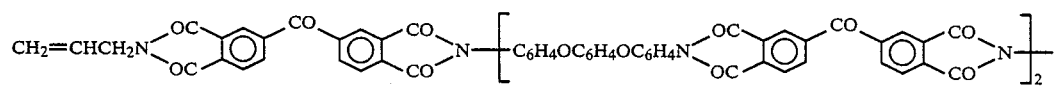

Polyimide DIENO #2

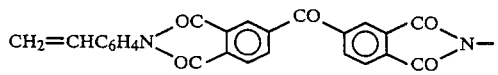

Polyimide DIENO #3

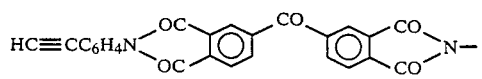

and the mixture refluxed for four hours or until no more water of reaction is formed. The product is isolated by the procedure of Example V and is found to be identical to Polyimide #2 of Example V.

EXAMPLE VII

Part I—Preparation of
$H_2NC_6H_4OC_6H_4SO_2C_6H_4OC_6H_4O_2SC_6H_4OC_6H_4NH_2$

This synthesis involves first the preparation of 4,4'-bis(4-chlorobenzenesulfonyl)diphenyl ether. Into a one liter round bottom flask, equipped with a stirrer, nitrogen inlet tube and reflux condenser, the top of which is attached to a bubbler and caustic absorber, is placed 165 grams (one mole) of diphenyl ether, 422 grams (two moles) of benzene sulfonyl chloride; and 16 grams (0.1 mole) of anhydrous ferric chloride. The mixture is heated slowly to 174° C. over a period of six hours during which time the deep green solution slowly thickens. At the end of this period, the material is poured into a beaker to cool. The crude product is crystallized from approximately two times its volume of acetone. This material is found to weigh 466 grams (90%). Recrystallization gives material having a melting point by DSC of 164° C. The second step is the preparation of 4-bis(4'-aminophenoxy)(4'',4'''-diphenylsulfonyl)ether (BAPP). Into a 500 ml. flask equipped with a stirrer, Dean-Stark trap and nitrogen inlet tube, is placed 66.1 grams (0.606 moles) of para-aminophenol, and 24 grams (0.6 mole) of sodium hydroxide dissolved in 25 ml. of water. Approximately 100 ml. of toluene and 100 ml. of dimethylsulfoxide are then added. This mixture is heated to reflux under nitrogen and the water removed by the Dean-Stark trap. When no more water is collected in the trap, toluene is distilled from the mixture and an additional 100 ml. of dimethylsulfoxide is added. To this solution is added 156.6 grams (0.30 moles) 4,4'-bis(4-chlorobenzenesulfonyl)diphenyl ether. This mixture is stirred under nitrogen while the temperature is brought to 160° C., which is maintained for one hour and 25 minutes, and then the product is cooled to room temperature. The resulting solution is then diluted with 2.5 liters of water and made basic (pH of ≈8) with sodium hydroxide. Precipitation of the crude product is accomplished upon addition of the sodium hydroxide. The precipitate is collected, washed with water, and redissolved in three liters of dilute hydrochloric acid. This solution is then slowly neutralized with sodium hydroxide to reprecipitate the product. After collecting the product on a Buchner funnel, it is washed again with cold water and dried in a vacuum to yield 131 grams (65%) of a creamed colored product having a DSC melting point of 265° C.

Part II—Preparation of Polyimide #3

The experimental procedure of Example VI is repeated except instead of DAPB-3,3', there is used 6.64 g. of BAPP. After reaction there is isolated an almost quantitative yield of:

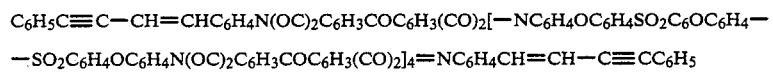

POLYIMIDE #3

The product is soluble in cresol, DMAC, DMF, DMSO, sulfolane and dioxane. The product becomes insoluble and infusible when heated at 250° C. The elemental analysis shows C: 69.34%, H: 3.14%, N: 3.07% which values are in excellent agreement for the calculated values for $C_{261}H_{146}N_{10}O_{53}S_8$.

EXAMPLE VIII

Preparation of Anhydride-Terminated Oligomeric Polyimide #3

Using the m-cresol-benzene azeotropic procedure, there is allowed to react BTCA (3.6251 g., 0.01125 mole) and DAPB-3,3 (2.9223 g., 0.01 mole) in 40 ml. of m-cresol and 10 ml. of benzene. There is obtained 5.6071 g. of polyimide #3 which is a light yellow powder soluble in m-cresol, DMAC, sulfolane and dioxane. On a Fisher-Johns melting point apparatus this melts at 120° C. with some evolution of gas. The TGA in air shows losses in air of 1% at 200° C.; 2% at 300° C.; 3% at 400° C.; 4% at 500° C. and 19% at 600° C. The elemental analysis shows 71.01% C, 3.22% H and 4.60% N, which values are in excellent agreement with the calculated values for the formula:

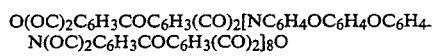

EXAMPLE IX

Preparation of Anhydride-Terminated Oligomeric Polyimide #4

Using the procedure of Example III, there is reacted BTCA (12.0827 g., 0.0375 mole) and 3,3'-sulfonyldianiline (SDA) (7.4493 g., 0.03 mole) in 80 ml. of m-cresol and 10 ml. of benzene. Polyimide #4 is obtained (16.9 g.) which is a light yellow solid, soluble in m-cresol, DMAC, SMF and sulfolane. The lowest temperature at which a sample melts completely when dropped onto a preheated block is 255° C. The TGA in air shows losses of 2% at 200° C.; 3% at 300° C.; 4% at 400° C.; 7% at 500° C.; and 26% at 600° C. The elemental analysis is 63.9% C. and 2.74% H, which values are in excellent agreement with the calculated values for the formula:

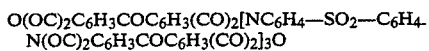

EXAMPLE X

Preparation of Anhydride-Terminated Polyimide #5

Using the procedure of Example III, BTCA (14.50 g., 0.045 mole) is reacted with SDA (9.9324 g., 0.04 mole) in 90 ml. of cresol and 20 ml. of benzene. Polyimide #5 is obtained (21.4 g.) which is a light yellow solid, soluble in m-cresol, DMAC, DMF and sulfolane. The lowest temperature at which a sample melts completely when dropped on a preheated block is 270° C. Its TGA in air shows losses of 0% at 200° C.; 2% at 300° C.; 4% at 500° C. and 25% at 600° C. The elemental analysis shows 63.99% C, 2.73% H and 4.95% N, which values are in good agreement with the calculated values for the formula:

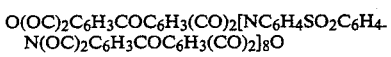

-continued

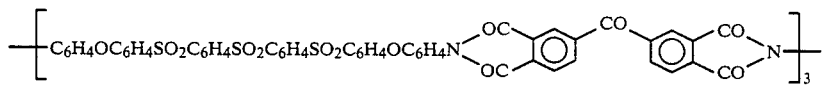

Polyimide DIENO #4

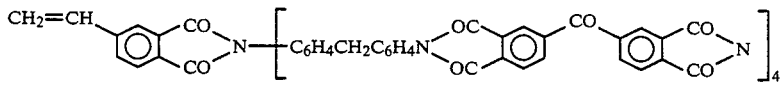

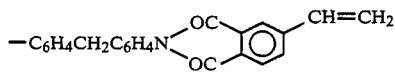

Polyimide DIENO #5

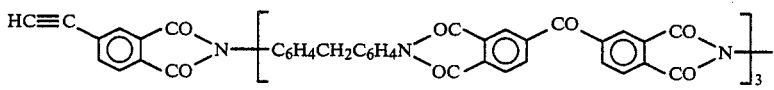

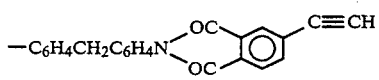

Polyimide DIENO #6

These dieno polyimides are blended thoroughly by grinding in a mortar with selected polyimides containing the terminal enyne groups of this invention. The mixtures spanned a wide range from 95 to 5; 50 to 50 and 5 to 95 moles percent of the two components as shown in the following tabulations:

| Mixture of Polyimides with Dieno-Imides | | |
|---|---|---|
| Addition Product | Polyimide Used # | Diene Used # | Mole Ratio |
| A | 1 | 1 | 95:5 |
| B | 1 | 1 | 50:50 |
| C | 1 | 1 | 5:95 |
| D | 2 | 2 | 95:5 |
| E | 2 | 2 | 5:95 |
| F | 2 | 3 | 50:50 |
| G | 3 | 3 | 50:50 |
| H | 4 | 4 | 50:50 |
| I | 6 | 4 | 50:50 |
| J | 8 | 1 | 50:50 |
| K | 12 | 5 | 50:50 |
| L | 12 | 4 | 50:50 |
| M | 15 | 6 | 95:5 |
| N | 15 | 6 | 5:95 |
| O | 15 | 6 | 95:5 |
| P | 18 | 5 | 5:95 |
| Q | 18 | 5 | 95:5 |

When these mixtures are heated at 275°–300° C. in a steel mold for 15 minutes, insoluble, infusible addition products are obtained in all cases.

EXAMPLE XVI

When a mixture of 95 parts by weight of polyimide #2

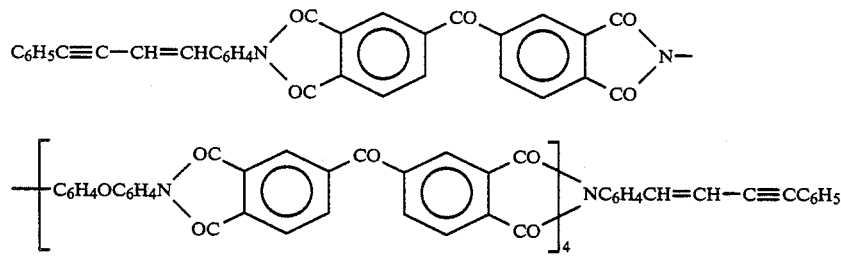

and five parts of $C_6H_5C{\equiv}C{-}C{\equiv}CC_6H_5$ are heated on a Fisher-Johns melting point apparatus, the softening point is lowered from about 252° C. to about 240° C., the viscosity of the melt is greatly reduced and the yield of insoluble, infusible product is quantitative.

The 1,4-diphenyl-buten-1-yne-3 is illustrative of diarylvinylacetylenes of the formula ArCH=CH—C≡CAr wherein Ar is the monovalent aryl group corresponding to the divalent Ar group of Formula I. Thus Ar represents an aromatic moiety containing at least 6 carbon atoms and preferably no more than 21 carbon atoms.

The melting or softening points, as well as the viscosity of polyimides #1, 3, 6, 9, 12, 13, 15 and 18 are similarly reduced by the addition of 5, 10 and 25 mole percent of $C_6H_5CH{=}CH{-}C{\equiv}CC_6H_5$ and $C_6H_5OC_6H_4CH{=}CH{-}C{\equiv}CC_6H_4OC_6H_5$, respectively. Also, the same degree of lowering of viscosity and melting points are observed by the addition of ArCH=CH—C≡CAr, specifically, $C_6H_5CH{=}CH{-}C{\equiv}CC_6H_5$ to the "Dieno" polyimides #1 to 6, inclusive. In all cases, insoluble, infusible addition products are obtained when the mixtures are heated to curing temperatures.

EXAMPLE XVII

To a 4.52 g. of polyimide #3 in 30 ml. of dioxane is added 0.3 g. of dimethyl diacetylene dicarboxylate and the mixture refluxed for two hours after which the dioxane is removed under vacuum at a pressure of 5 mm leaving the adduct in which the two terminal —CH=CH—C≡C—$C_6H_5$ groups have been converted to a phthalate derivative,

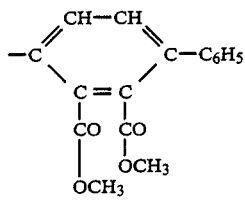

Appropriate tests confirm that there are two methyl carboxylate groups in the molecule. Replacement of the acetylene dicarboxylate by other dienophiles such as ethyl acrylate, diethyl acetylene dicarboxylate, styrene and N-phenyl maleimide also results in a Diels-Alder addition product.

EXAMPLE XVIII

The procedure of Example IV is repeated with appropriate modifications in the molar amount of benzophenone-tetracarboxylic acid anhydride (BTCA) to give an anhydride-terminated polyimide having a formula corresponding to anhydride-terminated polyimide #2 except that the n value is 18 instead of 4. Then this dianhydride is used in the procedure of Example V using the appropriate molar amount of $H_2NC_6H_4CH=CH—C≡CC_6H_5$ to give an imide derivative similar to that obtained in Example V except that the value of n in this imide derivative is 18 instead of 4. The procedure of Example V is repeated three times using the following as the vinylacetylene amines instead of that used in Example V:

a. $NH_2C_6H_4CH=CH—C≡CH$
b. $NH_2C_6H_4CH=CH—C≡CCH_3$
c. $NH_2C_6H_4CH=CH—C≡CC_6H_5$

The corresponding vinylacetylene-terminated polyimides of Formula I are obtained in which n has a value of 18. Reactions of equivalent amounts of these respective vinylacetylene-terminated polyimides with dienophiles in accordance with the materials and procedures of Examples XVI, XVII and XIX give results similar to those obtained in these respective examples.

EXAMPLE XIX

The procedure of Example V is repeated a number of times to prepare polyimides having terminal groups of the formula $RCH=C(R)—R'—N$ by reaction individually of polyimides #3, 4, 5, 6 and 7 each with the following amines respectively:

a. $NH_2CH_2C=CH_2$
b. $NH_2C_6H_4CH=CH_2$
c. $NH_2CH_2CH_2CH=CH_2$
d. $NH_2CH_2CH=CHCH_3$

In the above formula, R is as defined above, preferably hydrogen, methyl, phenyl or ethyl, and R' is a divalent radical to 1-20, preferably 1-10 carbon atoms including alkylene and arylene radicals including those defined above for Ar, preferably methylene, ethylene, propylene, phenylene, etc.

Each of these products is mixed with 5% and 25% by weight respectively of the following vinylacetylenes:

$C_6H_5—CH=CHC≡CC_6H_5$
$C_6H_5CH_2CH=CHC≡CCH_2C_6H_5$
$CH_3CH=CHC≡CCH_3$
$C_2H_5CH=CHC≡CC_2H_5$

In each case the resultant product when heated by itself or with a small amount of dicumyl peroxide gives an insoluble, infusible crosslinked polymer which is suitable for molding.

In some dienophiles there may be a single acetylenic or non-conjugated two or more acetylenic groups. To distinguish from the conjugated groups of this invention, these groups may be referred to as non-conjugated acetylenic groups.

While it is contemplated that the conjugated diacetylene-terminated polyimides of this invention are covered by the above Formula I, it is also contemplated that the polyimide between the two terminal groups may be interrupted by a joining group of a different type. For example, in preparing the polyimide inner structure, it is possible to use a diamine of the structure $H_2N—Ar—Z—ArNH_2$ in place of one or more molecules of the $H_2N—Ar—NH_2$ used in preparing the starting polyimide to which the terminal conjugated diacetylene groups are attached. In such case there are one or more Z groups in the inner part of the polymer molecules as well as in the terminal groups.

It is also contemplated that side branches may be formed by using a tri- or tetra-amino aromatic compound in place of small amounts of the diamine used in preparing the polyimide inner structure. Upon formation of the polyimide by reaction with the dianhydride, one or more side chains or branches will be formed so that ultimately there may be three or more terminals to which may be attached the conjugated diacetylene groups.

It is intended that these contemplated variations are included within the scope of the invention described herein.

For example, when the polyimide structure is prepared using $H_2NArZArNH_2$ as a portion of the diamine, there may be obtained a random copolymer in which the Z groups are distributed at random throughout the polyimide linear chain or may be in blocks, depending on how the Z-containing diamine is added. Thus if this diamine is admixed with one or more other diamines before the diamines are reacted with the dianhydride to form the polyimide, then a random copolymer will be produced. However, if the diamines are reacted separately, then block copolymers will be produced, possibly with homopolyimides of either or both types of diamines being present as byproducts. The dipolymers may be represented by the following formula:

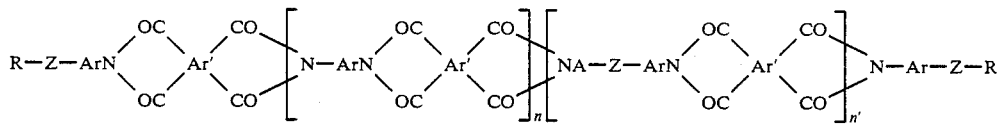

wherein R, Z, Ar, Ar', n and n' have the same definitions as given above.

As indicated above, the units within the n' brackets may be present as a single block or a plurality of blocks in a particular polymer molecule or may be dispersed at random between units of the type within the n brackets.

In the polyimide derivatives of this invention the Ar, Ar' and R groups are preferably hydrocarbon or hydrocarbon groups joined by various other groups as described above. However, there may also be various substituent groups present so long as they do not interfere with the reactions or functions described herein. The Ar and Ar' groups preferably comprise benzenoid radicals as illustrated.

Dienophiles that are reactive with the polyimides of this invention include those of the following formulas having the portion Q' which represents a polyimide portion of the formula:

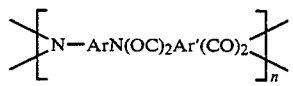

wherein the symbols have the same definitions as given above:

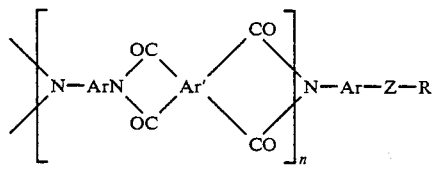

$CH_2=CHR'N(OC)_2Ar'(CO)_2=Q=N-R'CH=CH_2$
$R°C≡C-R'-N(OC)_2Ar'(CO)_2=Q=N-R'C≡CR°$
$R°C≡CAr''=(CO)_2=Q=NArN(OC)=Ar''C≡CR$
$R°C≡CHAr''=(CO_2)=Q=NArN(OC)-_2=Ar''CH=CR°$ and Ar'' is a trivalent aromatic radical having the same basic ring structure as Ar.

While certain features of this invention have been described in detail with respect to various embodiments thereof, it will of course be apparent that other modifications can be made within the spirit and scope of this invention, and it is not intended to limit the invention to the exact details insofar as they are defined in the following claims.

The invention claimed is:

1. The Diels-Alder addition product of a polyimide of the formula:

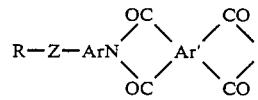

-continued

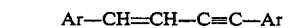

wherein:

Ar' is a tetravalent aromatic radical, the four carbonyl groups being attached directly to separate carbon atoms and each pair of carbonyl groups being attached to adjacent carbon atoms in Ar' except in the case of Ar' being a naphthlaene radical, one or both pairs of the carbonyl groups may be attached to peri-carbon atoms;

Ar is a divalent aromatic radical;

n is zero or an integer having a value of one to 20;

R is hydrogen or an organic moiety containing 1 to 21 carbon atoms;

Z is the structure $-CH=CH-C≡C-$ or $-C≡C-CH=CH-$;

and a dienophile of the formula:

$C_6H_5-C≡C-C≡C-C_6H_5$ or $Ar-CH=CH-C≡C-Ar$ wherein the Ar in the dienophile is a monovalent aromatic radical, the addition being between the enyne groups of the said polyimide, between the enyne groups of the polyimide and the $-C≡C-C≡C-$ or the $-CH=CH-C≡C-$ of the dienophile, and to a minor extent between the said enyne of the polyimide and any other unsaturation in an R group.

2. The addition product of claim 1, in which each R is H.

3. The addition product of claim 1, in which each R is $C_6H_5$.

4. The addition product of claim 1, in which each R is $CH_3$.

5. The addition product of claim 1, in which n is at least two.

6. The addition product of claim 1, in which n is at least three.

7. The addition product of claim 5, in which Ar' is a radical selected from the class consisting of:

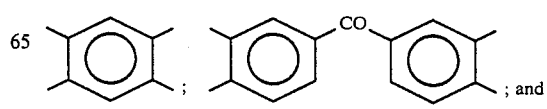

8. The addition product of claim 1, in which Ar' is

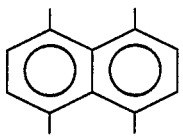

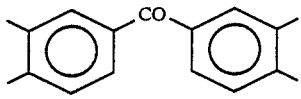

9. The addition product of claim 1, in which the Ar attached to Z is selected from the class consisting of —C$_6$H$_4$—, —C$_6$H$_4$OC$_6$H$_4$— and —C$_6$H$_4$SO$_2$C$_6$H$_4$—.

10. The addition product of claim 5, in which the Ar attached to Z is —C$_6$H$_4$—.

11. The addition product of claim 1, in which the polyimide is prepared by the reaction of a dianhydride of an aromatic tetracarboxylic acid and a diamine selected from the class consisting of:

1,3- and 1,4-(NH$_2$)$_2$ benzene;
2,3-; 2,4-; 2,6- and 3,5-(NH$_2$)$_2$-toluene;
3,3'-; 4,4'- and 3,4'-methylene dianiline;
4,4'-; 3,3'- and 3,4'-oxydianiline;
4,4'-; 3,3'- and 3,4'-sulfonyldianiline;
1,3-; 1,4- and 1,2-bis(3-aminophenoxy)benzene;
1,3- and 1,4-bis(4-aminophenoxy)benzene; and H$_2$NC$_6$H$_4$OC$_6$H$_4$SO$_2$C$_6$H$_4$OC$_6$H$_4$SO$_2$C$_6$H$_4$OC$_6$H$_4$NH$_2$
in which the respective attachments to a C$_6$H$_4$ ring are meta or para to each other.

12. The addition product of claim 11, in which the diamine used in preparing the original polyimide is a methylene dianiline.

13. The addition product of claim 11, in which the diamine used in preparing the original polyimide is a sulfonyl dianiline.

14. The addition product of claim 11, in which the diamine used in preparing the original polyimide is an oxydianiline.

15. The addition product of claim 11, in which the diamine used in preparing the original polyimide is 2,4-toluene diamine.

16. The addition product of claim 11, in which R is H.

17. The addition product of claim 11, in which R is C$_6$H$_5$.

18. The addition product of claim 1 in which n has a value of one to 10.

19. The addition product of claim 5 in which n has a value of one to 10.

20. The addition product of claim 7 in which n has a value of one to 10.

21. The addition product of claim 11 in which n has a value of one to 10.

22. The product of claim 1 in which the dienophile has the formula C$_6$H$_5$—CH=CH—C≡C—C$_6$H$_5$.

23. The product addition of claim 1 in which the dienophile has the formula C$_6$H$_5$—C≡C—C≡C—C$_6$H$_5$.

24. The product addition of claim 1 in which the dienophile has the formula C$_6$H$_5$—O—C$_6$H$_4$—CH=CH—C≡C—C$_6$H$_4$OC$_6$H$_5$.

* * * * *

UNITED STATES PATENT AND TRADEMARK OFFICE
CERTIFICATE OF CORRECTION

PATENT NO. : 4,520,198
DATED : May 28, 1985
INVENTOR(S) : Gaetano F. D'Alelio and Phillip A. Waitkus It is certified that error appears in the above-identified patent and that said Letters Patent is hereby corrected as shown below:

Col. 2, line 63, correct "-CH≡CXH" to read --- -C≡CX ---.

Col. 3, lines 15-23, in the formula correct

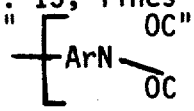

to read --- 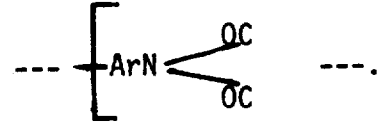 ---.

Col. 5, line 43, in the formula, correct "Ar" both appearances to read --- Ar' ---.

Col. 7, line 36, correct "-N-" to read --- -N̈- ---.

Col. 9, line 58, correct "N+1" to read --- n + 1 ---.

Col. 14, line 54, correct "-CA≡C-" to read --- -C≡C- ---.

Col. 15, lines 34-40, in the formula correct

"[-ArN⟨OC/OC-]"  to read  --- [-ArN⟨OC/OC-] ---.

UNITED STATES PATENT AND TRADEMARK OFFICE
CERTIFICATE OF CORRECTION

PATENT NO. : 4,520,198

DATED : May 28, 1985

INVENTOR(S) : Gaetano F. D'Alelio and Phillip A. Waitkus

It is certified that error appears in the above-identified patent and that said Letters Patent is hereby corrected as shown below:

Col. 19, line 34, before "polyimide" insert --- anhydride-terminated ---.
Col. 20, line 15, correct "#1" to read --- #2 ---.
Col. 20, lines 21 and 38, col. 22, line 11, and col. 23, lines 7 and 18, before "polyimide", in each appearance, insert --- anhydride-terminated ---.
Col. 22, lines 30 and 47, replace "Polyimide" in each appearance with --- Anhydride-terminated polyimide ---.
Col. 28, line 4, correct "to" to read --- of ---.
Col. 29, line 43, correct "Q'— Ar" to read --- Q'≡N-Ar ---.
Col. 29, lines 46, 47, 48 and 49, correct "Q" (in each appearance) to read --- Q' ---.

Signed and Sealed this

Eighth Day of October 1985

[SEAL]

Attest:

Attesting Officer

DONALD J. QUIGG

Commissioner of Patents and Trademarks—Designate